US011333777B2

United States Patent
Suwa et al.

(10) Patent No.: US 11,333,777 B2
(45) Date of Patent: May 17, 2022

(54) RADIATION IMAGING APPARATUS WITH IMPROVED IMPACT RESISTANCE

(71) Applicant: CANON KABUSHIKI KAISHA, Tokyo (JP)

(72) Inventors: Hidetomo Suwa, Machida (JP); Akiya Nakayama, Kawasaki (JP); Hiroto Kondo, Machida (JP); Masataka Suzuki, Yokohama (JP); Shichihei Sakuragi, Kawasaki (JP); Atsushi Takeuchi, Yokohama (JP); Riku Egawa, Kawasaki (JP); Tetsuo Watanabe, Utsunomiya (JP); Takaaki Gonda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/844,235

(22) Filed: Apr. 9, 2020

(65) Prior Publication Data

US 2020/0333483 A1    Oct. 22, 2020

(30) Foreign Application Priority Data

Apr. 19, 2019    (JP) .............................. JP2019-080006

(51) Int. Cl.
| | |
|---|---|
| *G01J 1/00* | (2006.01) |
| *G01T 7/00* | (2006.01) |
| *G01N 23/04* | (2018.01) |
| *A61B 6/00* | (2006.01) |
| *H04N 5/32* | (2006.01) |

(52) U.S. Cl.
CPC ................. *G01T 7/00* (2013.01); *A61B 6/42* (2013.01); *A61B 6/44* (2013.01); *G01N 23/04* (2013.01); *G01N 2223/30* (2013.01); *H04N 5/32* (2013.01)

(58) Field of Classification Search
CPC ....... G01T 7/00; G01T 1/20188; G01N 23/04; G01N 2223/30; A61B 6/44; A61B 6/42; A61B 6/4411; A61B 6/00; A61B 6/4405; H04N 5/32; G02B 43/02
See application file for complete search history.

(56) References Cited

U.S. PATENT DOCUMENTS 8,563,939 B2 * 10/2013 Okada .................... G03B 42/02
                                                250/370.09
8,901,505 B2    12/2014 Kobayashi et al.
(Continued)

FOREIGN PATENT DOCUMENTS

| JP | 2013072808 A | * | 4/2013 | ............... G01T 1/20 |
| JP | 5405778 B2 | | 2/2014 | |

(Continued)

*Primary Examiner* — Kiho Kim
(74) *Attorney, Agent, or Firm* — Canon U.S.A., Inc. I.P. Division

(57) ABSTRACT

A radiation imaging apparatus includes an internal unit having a radiation detector arranged to convert a radiation that is passed through a subject into electric signals. A base plate is arranged to support the radiation detector. A case having a rectangular parallelepiped shape is arranged to accommodate the internal unit. A fitting member is interposed between an inner wall of the case and an end portion of the internal unit, and fitted to the inner wall of the case and the end portion of the internal unit in a planar view as seen from an incident direction of the radiation.

20 Claims, 14 Drawing Sheets

(56) References Cited

U.S. PATENT DOCUMENTS

| | | | | |
|---|---|---|---|---|
| 2005/0056789 | A1* | 3/2005 | Spahn | H04N 5/321 250/370.09 |
| 2007/0152388 | A1* | 7/2007 | Utschig | F16F 7/00 267/136 |
| 2009/0202038 | A1* | 8/2009 | Wu | A61B 6/4429 378/62 |
| 2011/0024633 | A1* | 2/2011 | Aoyagi | G03B 42/04 250/361 R |
| 2013/0279660 | A1* | 10/2013 | Kikuchi | A61B 6/4405 378/91 |
| 2013/0341525 | A1* | 12/2013 | Maruta | G01T 1/17 250/394 |
| 2015/0293239 | A1* | 10/2015 | Miyoshi | A61B 6/4283 250/394 |
| 2015/0369930 | A1* | 12/2015 | Mruthyunjaya | H04N 5/32 250/370.08 |

FOREIGN PATENT DOCUMENTS

| | | | |
|---|---|---|---|
| JP | 2015062012 A | 4/2015 | |
| JP | 5827856 B2 | 12/2015 | |
| JP | 2016128790 A | 7/2016 | |

\* cited by examiner

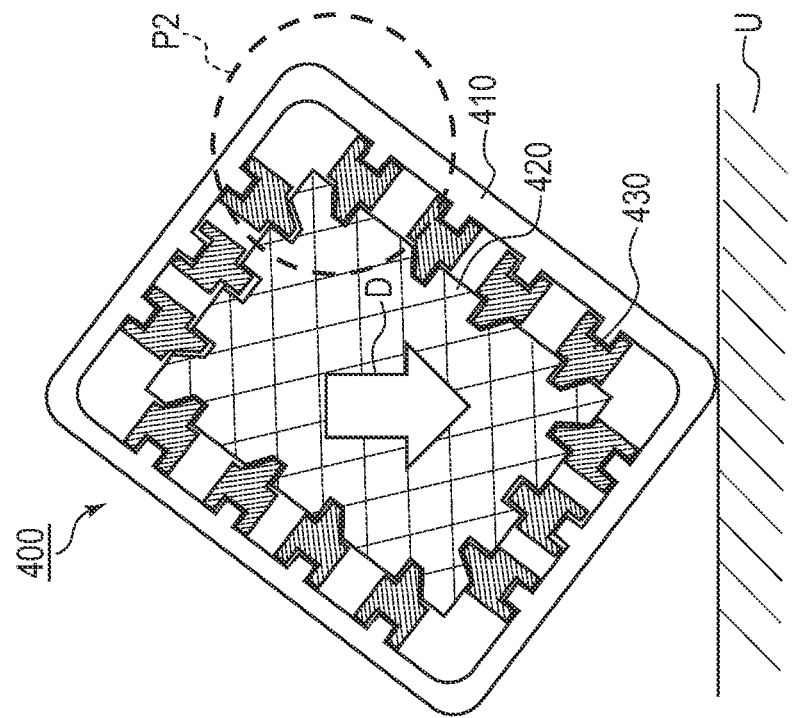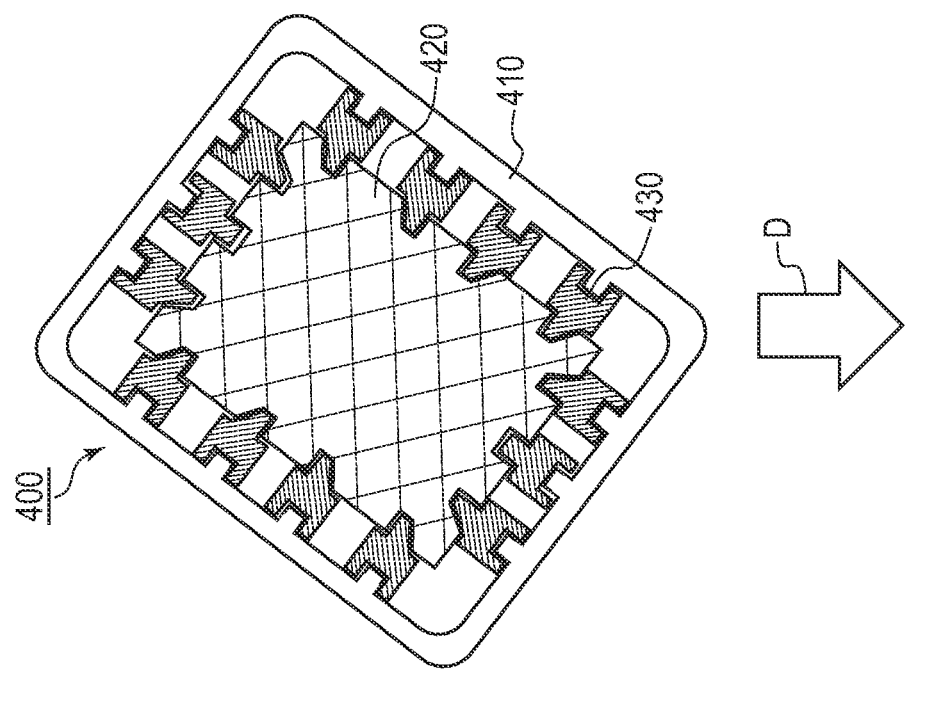

RADIATION IMAGING APPARATUS WITH IMPROVED IMPACT RESISTANCE

BACKGROUND OF THE INVENTION

Field of the Invention

The present disclosure relates to a radiation imaging apparatus configured to image a subject through use of a radiation. For example, the radiation imaging apparatus is suitable for application to a medical image diagnostic apparatus, a nondestructive inspection apparatus, and an analysis apparatus.

Description of the Related Art

There has been known an apparatus configured to obtain a radiation image of a subject by irradiating the subject with a radiation and detecting an intensity distribution of the radiation passed through the subject. In recent years, a method of obtaining a digital image through application of a digital technology and a semiconductor process technology is widely used. A radiation imaging apparatus adopting this method includes a radiation detector equipped with a semiconductor sensor having a desired area. The intensity distribution of the radiation is detected through conversion into electric signals by the radiation detector. The obtained electric signals are processed to acquire a radiation image, and the radiation image can be reproduced on a monitor or the like.

The radiation imaging apparatus are roughly classified into two types, specifically, a portable apparatus and a stationary apparatus. Of those apparatus, with regard to the portable apparatus, a person to be examined may get on the apparatus at the time of imaging, and the apparatus may fall off at the time of transport. Therefore, robustness is required for the portable apparatus.

In Japanese Patent No. 5827856, there is disclosed a technology of providing a buffer material between a radiation detector and a support base plate, to thereby alleviate an impact generated by falling or the like and protect the radiation detector. However, when the apparatus receives the impact, the buffer material exerts an impact-absorbing effect against an impact applied in a compression direction, but the impact-absorbing effect is not exerted against an impact applied in directions other than the compression direction.

Moreover, in Japanese Patent No. 5405778, there is disclosed a technology of providing a supporting mechanism at each corner portion of a radiation detector assembly provided inside an apparatus to bring the radiation detector assembly into abutment against a case, to thereby regulate movement of the radiation detector assembly. However, the supporting mechanism for merely bringing the radiation detector assembly into abutment against the case is only provided. Therefore, impact-absorbing performance against an impact generated by falling is insufficient.

SUMMARY OF THE INVENTION

The present disclosure has been made in view of such concerns and an aspect of the disclosure is to provide a radiation imaging apparatus which is improved in impact resistance against an impact generated by falling and is enhanced in protection of a radiation detector provided inside the radiation imaging apparatus.

According to an aspect of the present disclosure, there is provided a radiation imaging apparatus including an internal unit which includes a radiation detector arranged to convert a radiation that is passed through a subject into electric signals. A base plate is arranged to support the radiation detector, a case having a rectangular parallelepiped shape and arranged to accommodate the internal unit. A fitting member is interposed between an inner wall of the case and an end portion of the internal unit, and fitted to the inner wall of the case and the end portion of the internal unit in a planar view as seen from an incident direction of the radiation.

Further features and aspects of the present disclosure will become apparent from the following description of example embodiments with reference to the attached drawings.

BRIEF DESCRIPTION OF THE DRAWINGS

FIG. 9A and FIG. 9B are views for illustrating an example of a state in which a corner portion of the radiation imaging apparatus illustrated in FIG. 8 falls in a vertical direction toward the floor.

DESCRIPTION OF THE EMBODIMENTS

Numerous embodiments and various features of the present disclosure will now be described in detail in accordance with the accompanying drawings.

In the following description, the term "radiation" is not limited to an X-ray and encompasses an α-ray, a β-ray, a γ-ray, a particle beam, a cosmic ray, and the like.

First Example Embodiment

Figure 1:
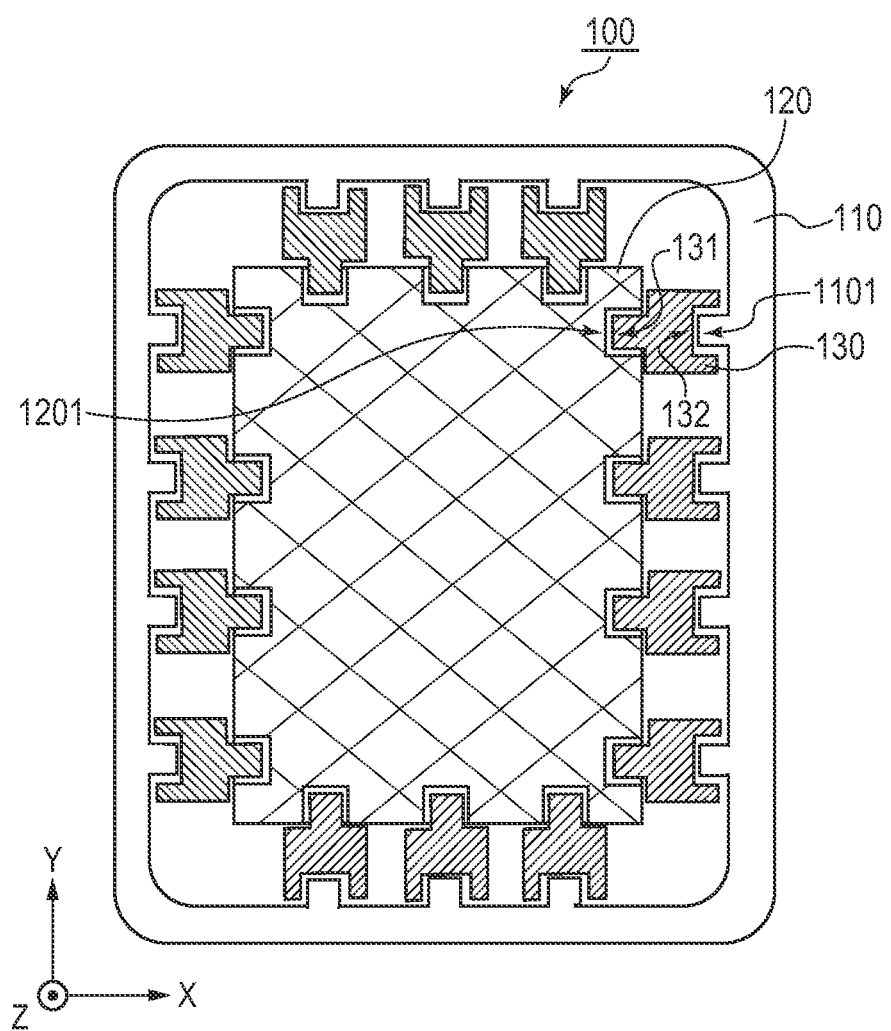
FIG. 1 is a view for illustrating an example of an internal configuration of a radiation imaging apparatus according to a first example embodiment of the present disclosure as seen from a back surface side.

A first example embodiment will herein now be described. FIG. 1 is an illustration of an internal configuration of a portable radiation imaging apparatus (hereinafter referred to as "imaging apparatus") 100 as seen from a side of a back surface which is located on a side opposite to an incident surface (side opposed to the incident surface) on which the radiation is incident. In FIG. 1, an XYZ coordinate system is illustrated. The Z-axis represents an incident direction of the radiation passed through a subject. The X-axis and the Y-axis represent two axes being orthogonal to the Z-axis and being orthogonal to each other. All of other XYZ coordinate systems illustrated in other drawings are consistent with the XYZ coordinate system illustrated in FIG. 1.

The imaging apparatus 100 includes an exterior case 110, an internal unit 120, and fitting members 130. The internal unit 120 includes a radiation detector (hereinafter referred to as "detector") 121 and a base plate 124 (see FIG. 2A and FIG. 2B). The detector 121 is arranged to convert a radiation passed through a subject into electric signals. The base plate 124 is arranged to support the detector 121. Moreover, end portions of the internal unit 120 each have a plurality of recesses (first recess) 1201. The exterior case 110 has a rectangular parallelepiped shape and is arranged to accommodate the internal unit 120 and the fitting members 130. Moreover, inner walls of the exterior case 110 each have a plurality of protrusions (first protrusion) 1101. The fitting members 130 are interposed between the inner walls of the exterior case 110 and the end portions of the internal unit 120 and are fitted to the inner walls of the exterior case 110 and the end portions of the internal unit 120 in a planar view as seen from the incident direction of the radiation (hereinafter referred to as "XY planar view"). The fitting members 130 each have a protrusion (second protrusion) 131 and a recess (second recess) 132. The protrusions 131 are fitted to the recesses (first recess) 1201 formed in the end portions of the internal unit 120, and the recesses 132 are fitted to the protrusions (first protrusion) 1101 formed on the inner walls of the exterior case 110. The fitting members 130 function as movement regulating members arranged to regulate movement of the internal unit 120. The fitting members 130 are arranged to regulate movement of the internal unit 120 in an in-plane direction within an XY plane and fix a position of the internal unit 120.

Moreover, the internal unit 120 has a substantially quadrilateral shape in the XY planar view. A plurality of fitting members 130 are arranged at all of four sides (upper, lower, right, and left sides) except corner portions of the substantially quadrilateral shape of the internal unit 120 (preferably, two to four fitting members 130 at each of short sides, and three to six fitting members 130 at each of long sides).

Figure 2A:
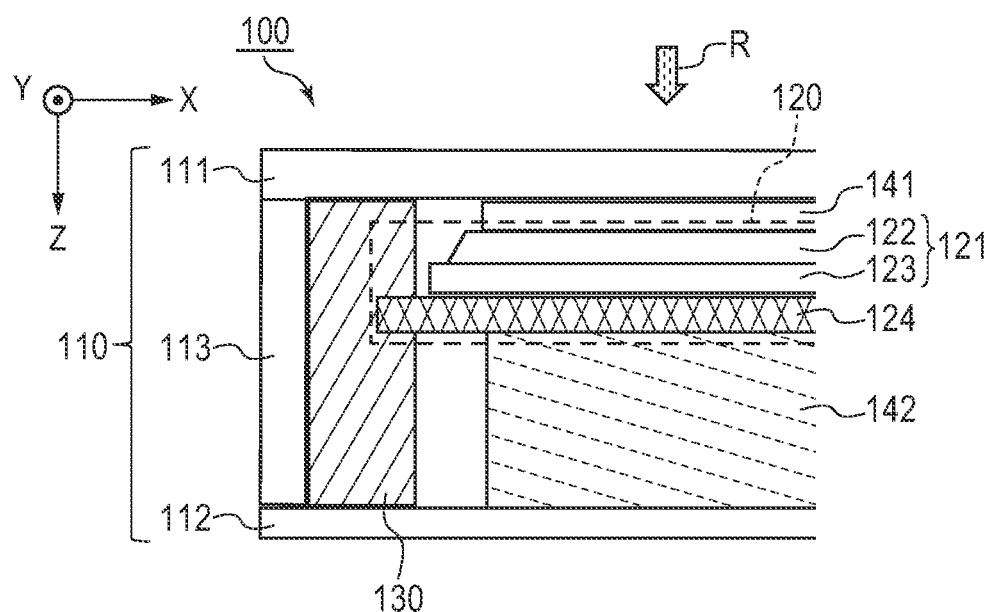
FIG. 2A and FIG. 2B are partial sectional views for illustrating an example of an internal configuration of the radiation imaging apparatus illustrated in FIG. 1 on different XZ cross sections.
Figure 2B:
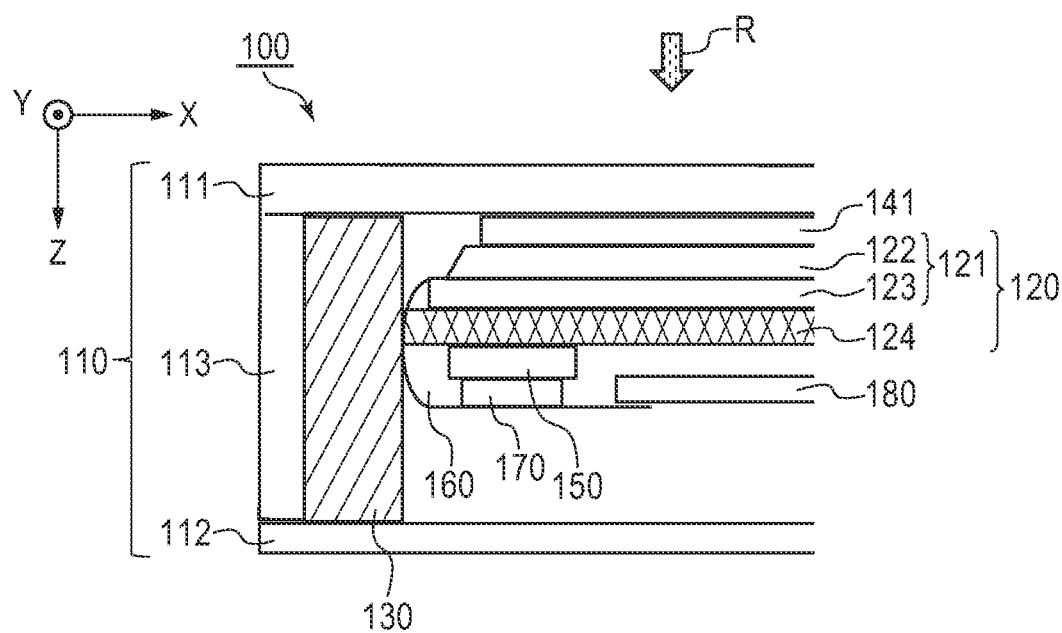

FIG. 2A and FIG. 2B are partial sectional views for illustrating an internal configuration of the imaging apparatus 100 illustrated in FIG. 1 on different XZ cross sections. In each drawing, the same members are denoted by the same reference symbols, and a detailed description thereof is omitted.

As illustrated in FIG. 2A, the exterior case 110 includes an incident-side case portion 111, a back-surface-side case portion 112, and a side-surface-side case portion 113. The incident-side case portion 111 forms an incident surface on which a radiation R is incident. The back-surface-side case portion 112 forms a back surface located on a side opposite to the incident surface. The side-surface-side case portion 113 forms a side surface. The back-surface-side case portion 112 and the side-surface-side case portion 113 may be formed integrally with each other. The incident-side case portion 111 is made of a material such as CFRP having high transmittance for the radiation (X-ray) R. The side-surface-side case portion 113 and the back-surface-side case portion 112 are made of a material such as an aluminum alloy or a magnesium alloy having small weight and high strength. However, depending on a specification of the apparatus, the CFRP or a resin may be used for the side-surface-side case portion 113 and the back-surface-side case portion 112.

The detector 121 includes a fluorescent body (scintillator) 122 and a photoelectric conversion element 123. The fluorescent body 122 is arranged to convert the incident radiation R into light. For protection of the fluorescent body 122, the fluorescent body 122 can be covered with a protection layer. The photoelectric conversion element 123 is typically formed of a glass substrate having a semiconductor sensor mounted thereon and is arranged to convert the light generated by the fluorescent body 122 into electric signals (analog electric signals). Moreover, a blocking member (not shown) having a function to block the incident radiation R may be provided between the detector 121 and the base plate 124. For example, a heavy metal such as lead or tungsten may be used for the blocking member. When the blocking member is provided, an artifact of a radiation image acquired by the imaging apparatus 100 can be reduced, and an electric board can be protected from the radiation R.

A buffer material 141 has high radiation transmittance and has a role of protecting the detector 121 from an impact from the incident surface or a local load. A support member 142 is provided between the internal unit 120 and the back-surface-side case portion 112 and is arranged to support various components present inside the exterior case 110. The support member 142 is formed so as to fill a space between the various components present inside the exterior case 110 and the back-surface-side case portion 112. However, the support member 142 is not limited to this mode and may be in the following mode. Specifically, for example, a plurality of members each having a columnar structure are arranged as support members 142, and a power supply for driving the detector 121, an electric board for performing signal processing on the electric signals transmitted from the detector 121, and other components may be provided in a gap defined by the plurality of support members 142.

As illustrated in FIG. 2B, in addition to the internal unit 120 and the fitting members 130, a buffer material 150, flexible boards 160, IC boards 170, and an electric board 180 are provided inside the exterior case 110. The analog electric signals generated by the photoelectric conversion element 123 are input to the IC boards 170 via the flexible boards 160 and are converted into digital electric signals by the IC boards 170. Further, the digital electric signals are converted into image signals by the electric board 180 and a signal processing board 190 illustrated in FIG. 3 so that a radiation image is generated based on the image signals.

Figure 3:
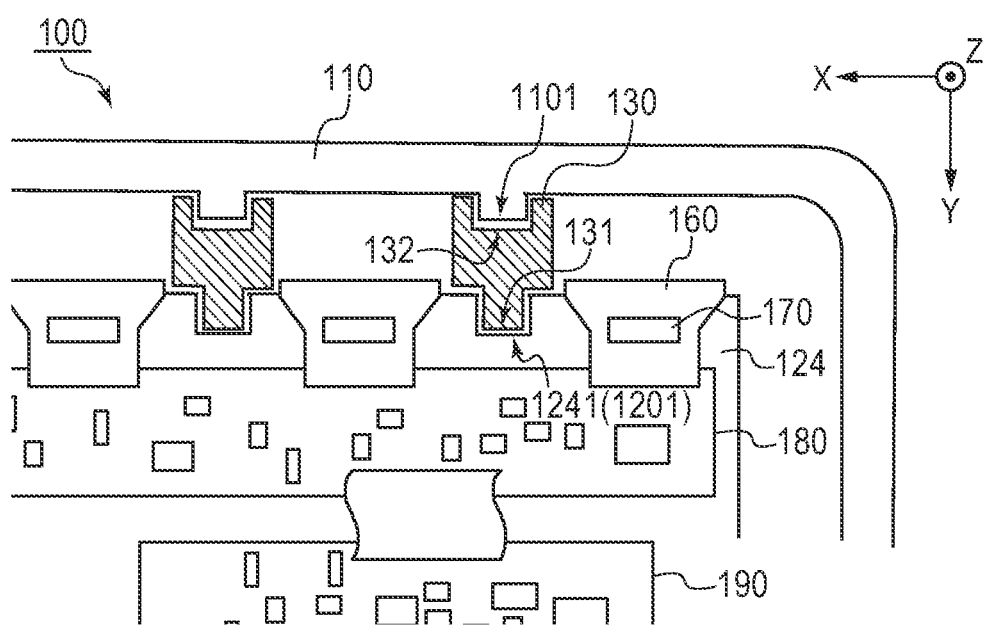
FIG. 3 is a view for illustrating an example of an internal configuration of the radiation imaging apparatus illustrated in the partial sectional view of FIG. 2B as seen from the back surface side.

FIG. 3 is a view for illustrating the imaging apparatus 100 illustrated in the partial sectional view of FIG. 2B as seen from the back surface side. In FIG. 3, the signal processing board 190 described above is illustrated in addition to the internal configuration illustrated in FIG. 2B.

In FIG. 2B, illustration is given such that the flexible board 160 is located between the fitting member 130 and the base plate 124. However, in actuality, as illustrated in FIG. 3, the fitting members 130 are each provided between a plurality of flexible boards 160 so as to prevent interference with the flexible boards 160.

Moreover, the fitting members 130 each have the protrusion 131 and the recess 132 in the XY planar view. The protrusions 131 are fitted to recesses 1241 formed in end portions of the base plate 124. Here, the recesses 1241 formed in the end portions of the base plate 124 illustrated in FIG. 3 correspond to the recesses 1201 formed in the end portions of the internal unit 120 illustrated in FIG. 1. The recesses 132 are fitted to the protrusions 1101 formed on the inner walls of the exterior case 110.

Figure 4A:
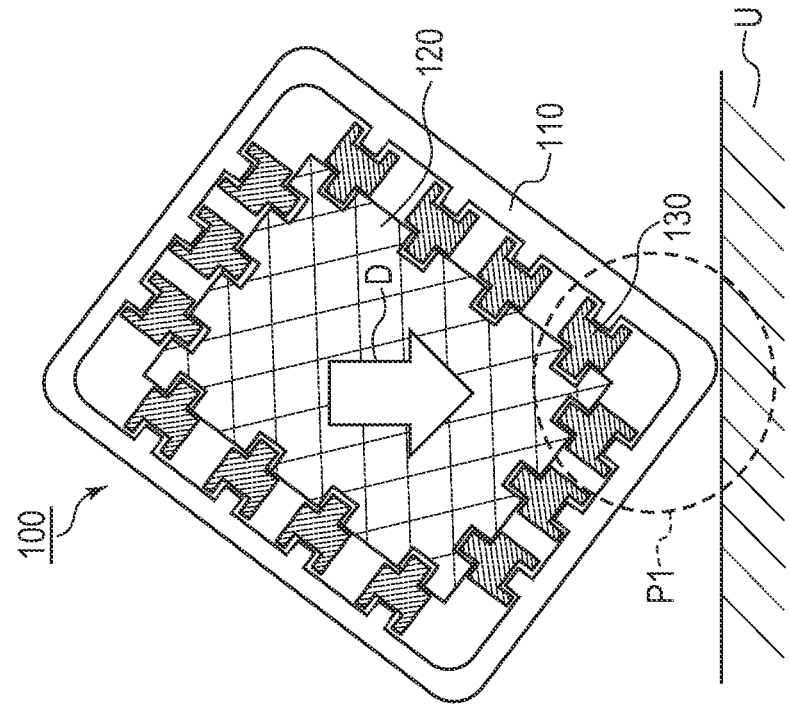
FIG. 4A and FIG. 4B are views for illustrating an example of a state in which a corner portion of the radiation imaging apparatus illustrated in FIG. 1 falls in a vertical direction toward a floor.
Figure 4B:
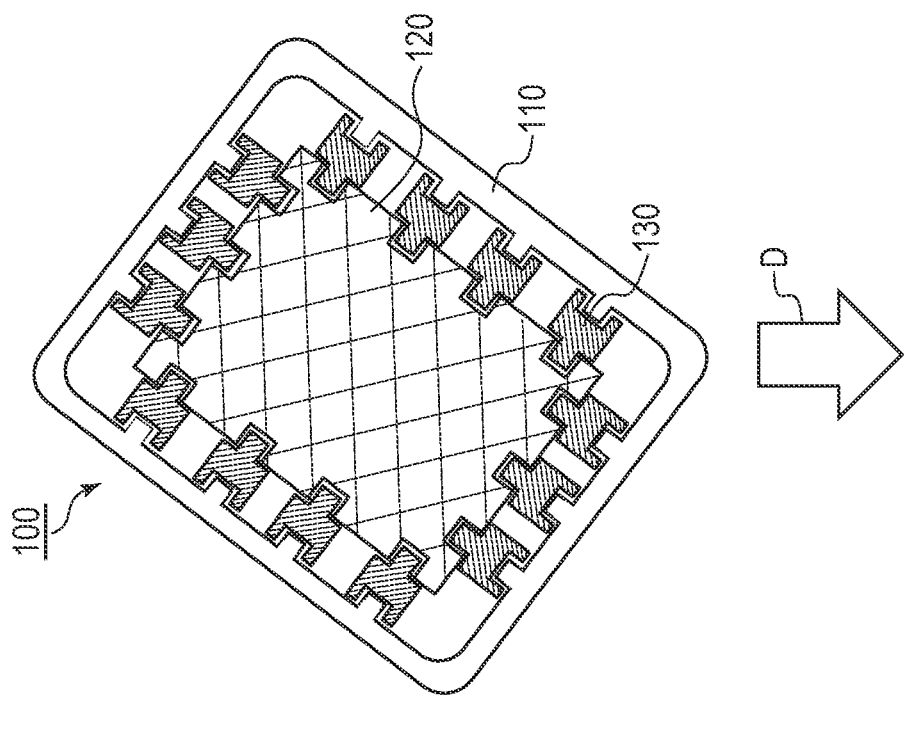

FIG. 4A is an illustration of a state in which the imaging apparatus 100 is falling. FIG. 4B is an illustration of a state in which a corner portion of the imaging apparatus 100 is in contact with a floor surface of a floor U. Here, for the sake of description, similarly to FIG. 1, illustration is given of the internal configuration of the imaging apparatus 100 as seen from the back surface side. However, in actuality, the back-surface-side case portion 112 illustrated in FIG. 2A and FIG. 2B is mounted to the imaging apparatus 100.

Figure 5A:
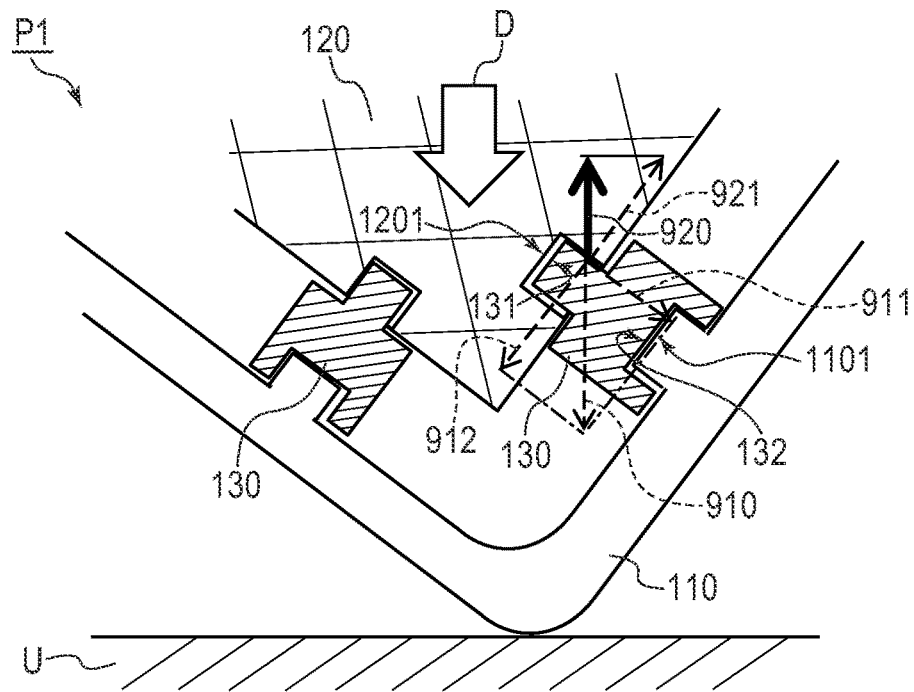
FIG. 5A and FIG. 5B are enlarged views for illustrating the portion of the region P1 illustrated in FIG. 4B.
Figure 5B:
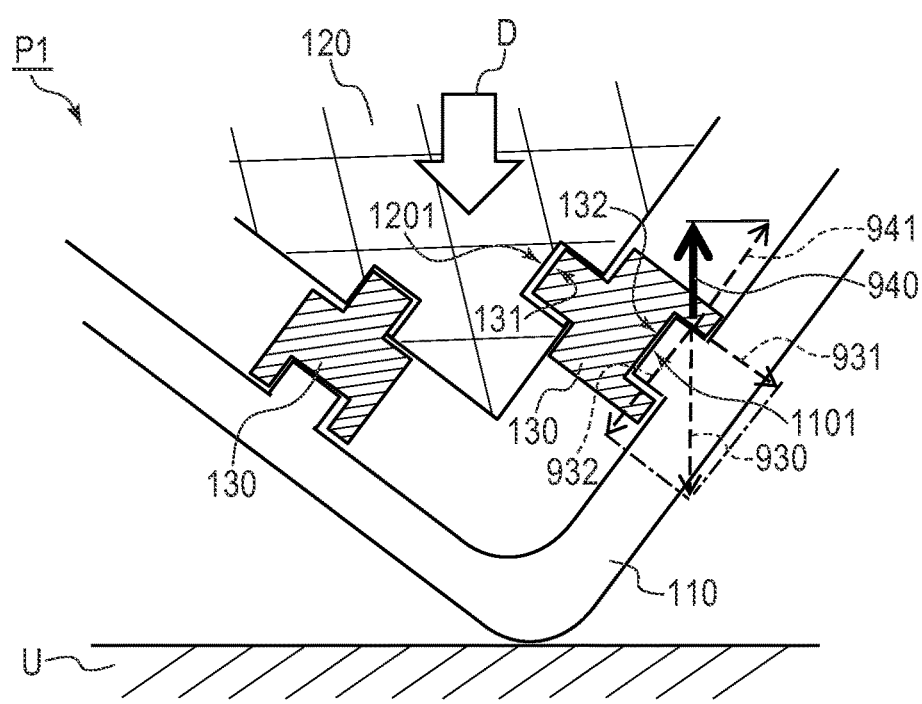

FIG. 5A and FIG. 5B are enlarged views for illustrating the portion of the region P1 illustrated in FIG. 4B.

First, FIG. 5A is described. At the moment at which the imaging apparatus 100 is brought into contact at its corner portion with the floor surface of the floor U as a result of falling, the internal unit 120 is forced to move in the falling direction (that is, vertical direction D) by an inertial force acting thereon. At this time, a stress 910 may be generated in the fitting member 130. The stress 910 is a resultant force of a component force 911 and a component force 912. The protrusion 131 of the fitting member 130 is fitted to the recess 1201 of the internal unit 120. With this, a reaction force 920 is generated, and the inertial force acting on the internal unit 120 is received, thereby being capable of regulating the movement of the internal unit 120. Moreover, a reaction force 921 against the component force 912 also contributes to the movement regulation.

Next, FIG. 5B is described. As described above, at the moment at which the imaging apparatus 100 is brought into contact at its corner portion with the floor surface of the floor U as a result of falling, the internal unit 120 is forced to move in the falling direction (that is, vertical direction D) by the inertial force acting thereon. At this time, a stress 930 may also be generated in the fitting member 130. The stress 930 is a resultant force of a component force 931 and a component force 932. The recess 132 of the fitting member 130 is fitted to the protrusion 1101 of the exterior case 110. With this, a reaction force 940 is generated, and the inertial force acting on the internal unit 120 is received, thereby being capable of regulating the movement of the internal unit 120. Moreover, a reaction force 941 against the component force 932 also contributes to the movement regulation.

The photoelectric conversion element 123 is formed of a glass substrate in many cases. When the movement of the internal unit 120 can be regulated, breakage of the glass substrate is prevented. As a result, damage on the photoelectric conversion element 123 can be prevented.

Moreover, when the plurality of fitting members 130 are arranged at all of the four sides (upper, lower, right, and left sides) of the substantially quadrilateral shape of the internal unit 120, the inertial force generated by the impact of falling or the like can be received in a distributed manner at a plurality of positions at which the fitting members 130 are arranged, thereby being capable of more effectively preventing the movement of the internal unit 120.

A gap defined between the recess 1201 and the protrusion 131 can be set as small as possible for impact resistance.

Second Example Embodiment

Next, a second example embodiment of the present disclosure is described. In the following description of the second embodiment, a description of matters which are common to the first embodiment described above is omitted, and matters different from those of the first embodiment are described.

Figure 6:
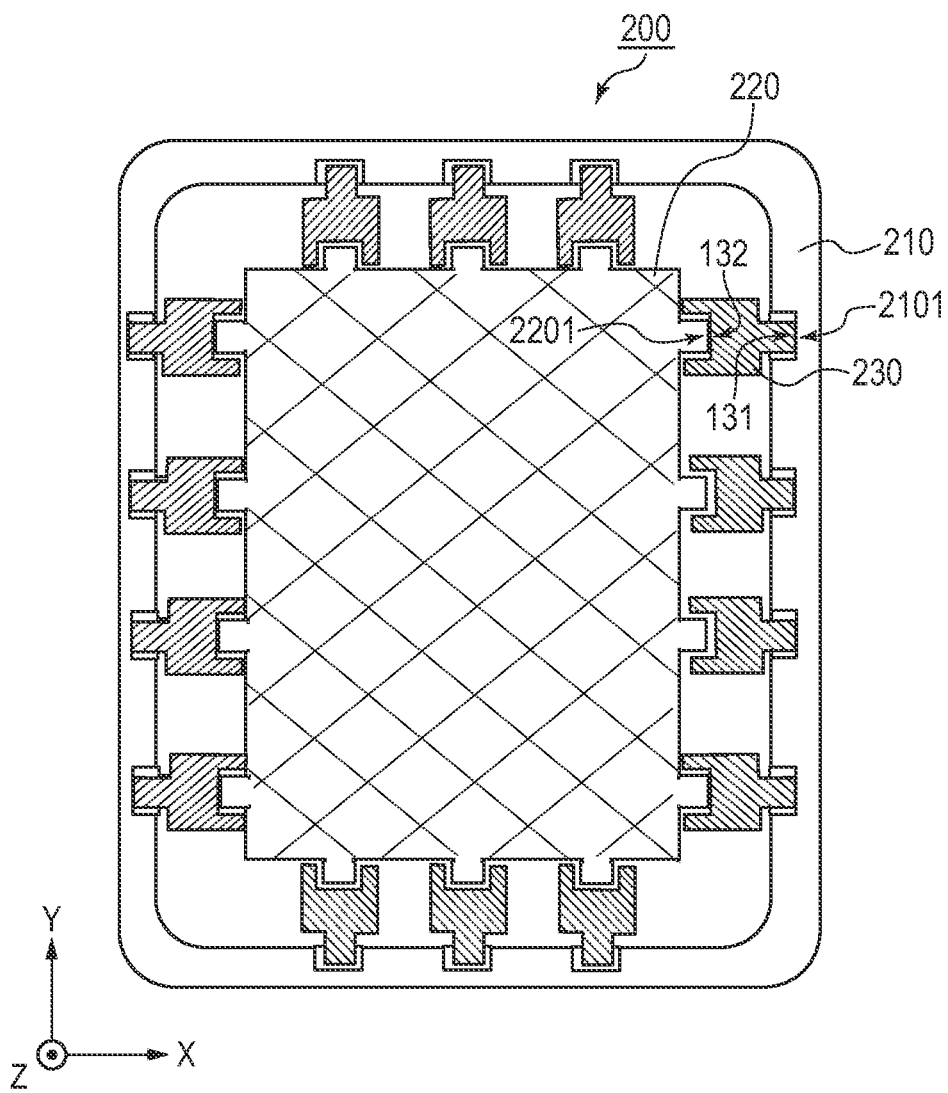
FIG. 6 is a view for illustrating an example of an internal configuration of a radiation imaging apparatus according to a second example embodiment of the present disclosure as seen from a back surface side.

FIG. 6 is a view for illustrating an internal configuration of an imaging apparatus 200 as seen from a back surface side.

An exterior case 210 corresponds to the exterior case 110 illustrated in FIG. 1 but is different from the exterior case 110 in that the exterior case 210 has a plurality of recesses (first recess) 2101 formed in inner walls thereof.

An internal unit 220 corresponds to the internal unit 120 illustrated in FIG. 1 but is different from the internal unit 120 in that the internal unit 220 has a plurality of protrusions (first protrusion) 2201 formed on end portions thereof. The internal unit 220 includes the detector 121 and the base plate 124. However, in the second embodiment, protrusions corresponding to the protrusions 2201 formed on the end portions of the internal unit 220 are formed on the end portions of the base plate 124.

Fitting members 230 correspond to the fitting members 130 illustrated in FIG. 1. Similarly to the fitting members 130, the fitting members 230 each have the protrusion (second protrusion) 131 and the recess (second recess) 132. The protrusions 131 are fitted to the recesses (first recess) 2101 formed in the inner walls of the exterior case 210, and the recesses 132 are fitted to the protrusions (first protrusion) 2201 formed on the end portions of the internal unit 220. The first embodiment and the second embodiment are reversed in the relationship between the protrusions and the recesses.

Moreover, the imaging apparatus 200 may include the buffer material 141, the support member 142, the buffer material 150, the flexible boards 160, the IC boards 170, the electric board 180, and the signal processing board 190 inside the exterior case 210.

Moreover, in the exterior case 110, 210, an interface for connecting a switch and a communication cable may be provided. The shape of the internal unit 120, 220 and the shape of the exterior case 110, 210 are not uniform. Therefore, orientations may be changed depending on positions at which the fitting members 130, 230 are provided, and the number of protrusions and recesses and widths thereof may be changed.

Third Example Embodiment

Next, a third example embodiment of the present disclosure is described. In the following description of the third embodiment, a description of matters which are common to the first and second embodiments described above is omitted, and matters different from those of the first and second embodiments are described.

Figure 7:
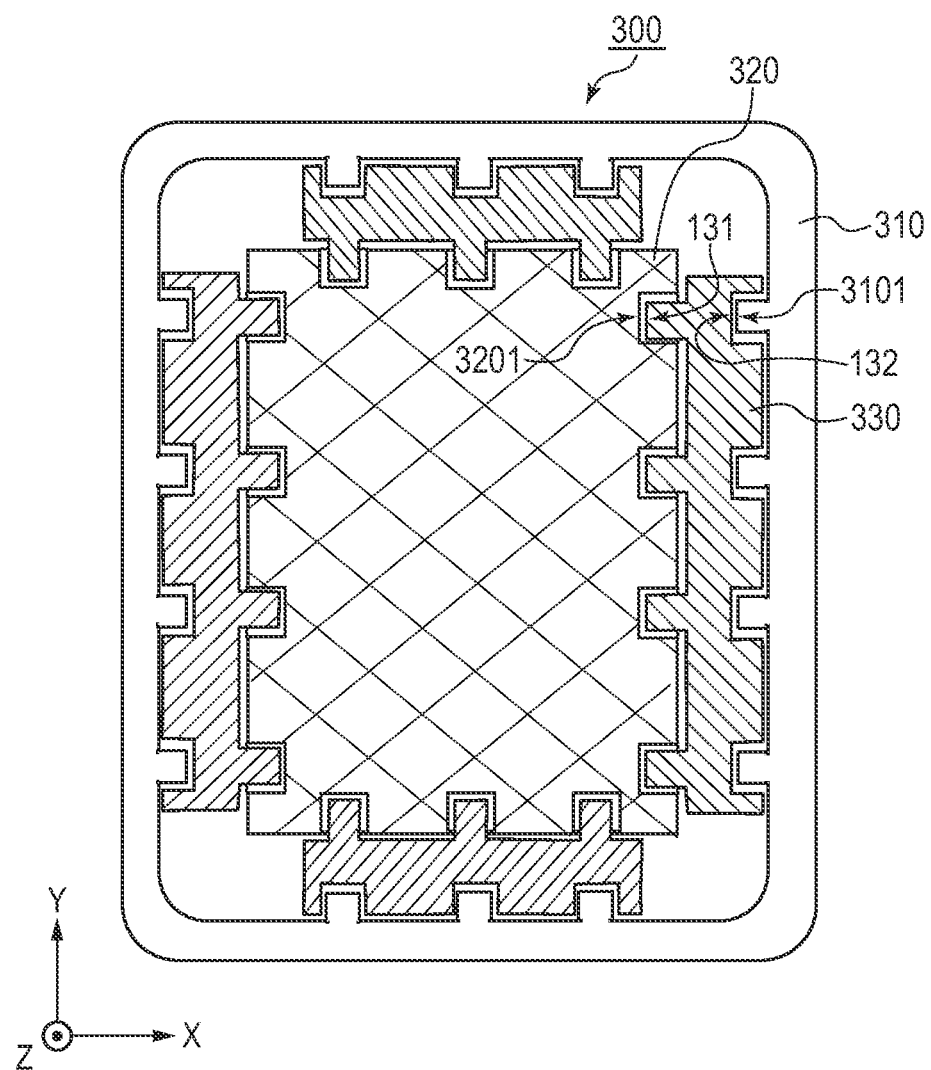
FIG. 7 is a view for illustrating an example of an internal configuration of a radiation imaging apparatus according to a third example embodiment of the present disclosure as seen from a back surface side.

FIG. 7 is a view for illustrating an internal configuration of an imaging apparatus 300 as seen from a back surface side.

An exterior case 310 corresponds to the exterior case 110 illustrated in FIG. 1 and has a plurality of protrusions (first protrusion) 3101 formed on inner walls thereof.

An internal unit 320 corresponds to the internal unit 120 illustrated in FIG. 1 and has a plurality of recesses (first recess) 3201 formed in end portions thereof.

Fitting members 330 correspond to the fitting members 130 illustrated in FIG. 1 but are different from the fitting members 130 in that each fitting member 330 has a plurality of protrusions (second protrusion) 131 and a plurality of recesses (second recess) 132. That is, the fitting members 330 are each formed by integrating the plurality of fitting members 130 arranged at each of four sides of the internal unit 120 illustrated in FIG. 1. A fitting method is the same as the first embodiment described above, and hence a detailed description thereof is omitted.

The fitting members 330 may be applicable also in a mode of setting a reversed relationship between the protrusions and the recesses and fitting the fitting members 330 to the exterior case 210 and the internal unit 220 illustrated in FIG. 6.

An example in which the same number of protrusions 131 as the recesses 3201 of the internal unit 320 and the same number of recesses 132 as the protrusions 3101 of the exterior case 310 are formed is described. However, in the third embodiment, it is not always required that the numbers be the same, and different numbers may be given depending on an internal structure of the imaging apparatus 300.

Fourth Example Embodiment

Next, a fourth example embodiment of the present disclosure is described.

In the following description of the fourth embodiment, a description of matters which are common to the first to third embodiments described above is omitted, and matters different from those of the first to third embodiments are described.

Figure 8:
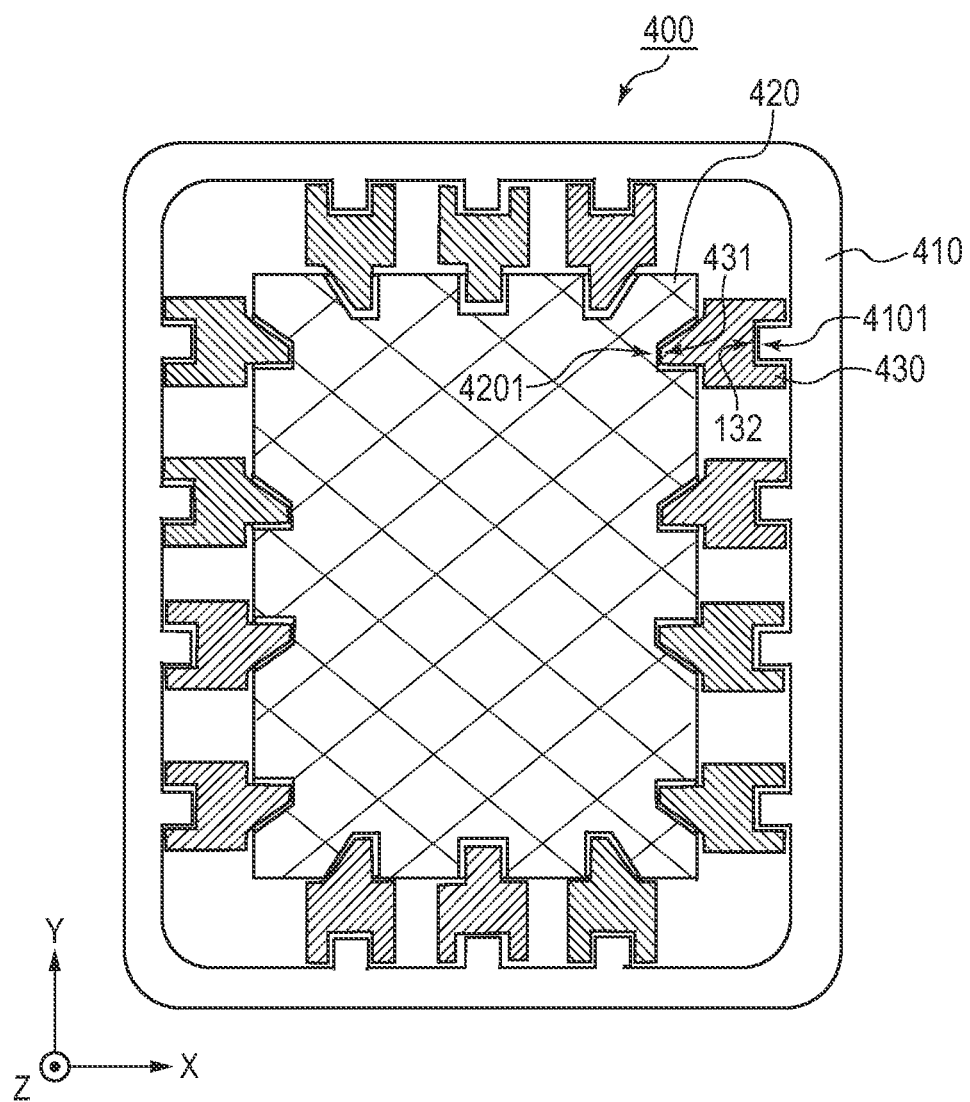
FIG. 8 is a view for illustrating an example of an internal configuration of a radiation imaging apparatus according to a fourth example embodiment of the present disclosure as seen from a back surface side.

FIG. 8 is a view for illustrating an internal configuration of an imaging apparatus 400 as seen from a back surface side.

An exterior case 410 corresponds to the exterior case 110 illustrated in FIG. 1 and has a plurality of protrusions (first protrusion) 4101 formed on inner walls thereof.

An internal unit 420 corresponds to the internal unit 120 illustrated in FIG. 1 and has a plurality of recesses (first recess) 4201 formed in end portions thereof. However, the internal unit 410 is different from the internal unit 120 in that a part of a side wall in each of the recesses 4201 of the internal unit 420 is inclined. Moreover, the internal unit 420 includes the detector 121 and the base plate 124 and has the recesses 4201, in which a part of the side wall is inclined, formed in the end portions of the base plate 124.

Fitting members 430 correspond to the fitting members 130 illustrated in FIG. 1 and each have a protrusion (second protrusion) 431 and the recess (second recess) 132. However, the fitting members 430 are different from the fitting members 130 in that the protrusion 431 of the fitting member 430 is inclined at a portion to be fitted to the inclined part of the side wall in the recess 4201 of the base plate 124. A fitting method is the same as the first embodiment described above, and hence a detailed description thereof is omitted.

Similarly to FIG. 4A, FIG. 9A is an illustration of a state in which the imaging apparatus 400 is falling. Similarly to FIG. 4B, FIG. 9B is an illustration of a state in which a corner portion of the imaging apparatus 400 is in contact with the floor surface of the floor U.

Figure 10:
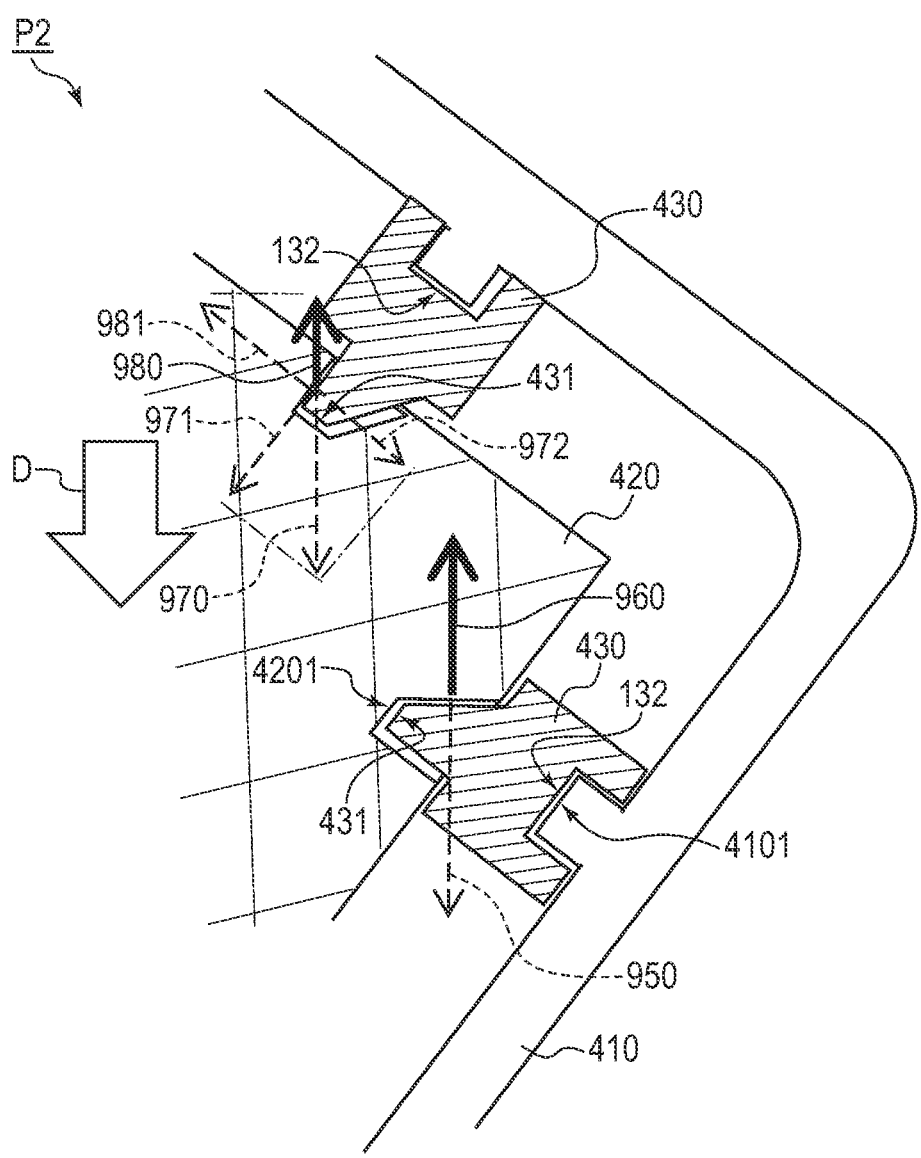
FIG. 10 is an enlarged view for illustrating the portion of the region P2 illustrated in FIG. 9B.

FIG. 10 is an enlarged view for illustrating the portion of the region P2 illustrated in FIG. 9B.

At the moment at which the imaging apparatus 400 is brought into contact at its corner portion with the floor surface of the floor U as a result of falling, a stress 950 may be generated in the fitting members 430. The fitting member 430 has such a shape that a part of a side wall of the protrusion 431 is inclined, and a part of the side wall of the recess 4201 of the internal unit 420 to which the protrusion 431 is to be fitted also has such a shape of being inclined in conformity with the shape of the fitting member 430. In FIG. 10, an example in which an angle of falling and an angle of the inclination are optimized is illustrated. In this case, a reaction force 960 is generated against the stress 950 generated in the fitting member 430 without generation of a component force. The stress 950 and the reaction force 960 have the same magnitude. With such a shape, movement of the internal unit 420 at the time of falling can be prevented more reliably.

Moreover, a portion of the side wall of the protrusion 431 having no inclination is brought into contact with a portion of the side wall of the recess 4201 of the internal unit 420 having no inclination. A component force 971 and a component force 972 of a stress 970 are generated in the fitting member 430. Moreover, a reaction force 980 corresponding to the reaction force 920 is generated, and a reaction force 981 against the component force 972 is also generated.

Fifth Example Embodiment

In the following description of a fifth example embodiment of the present disclosure, a description of matters which are common to the first to fourth embodiments described above is omitted, and matters different from those of the first to fourth embodiments are described.

Figure 11A:
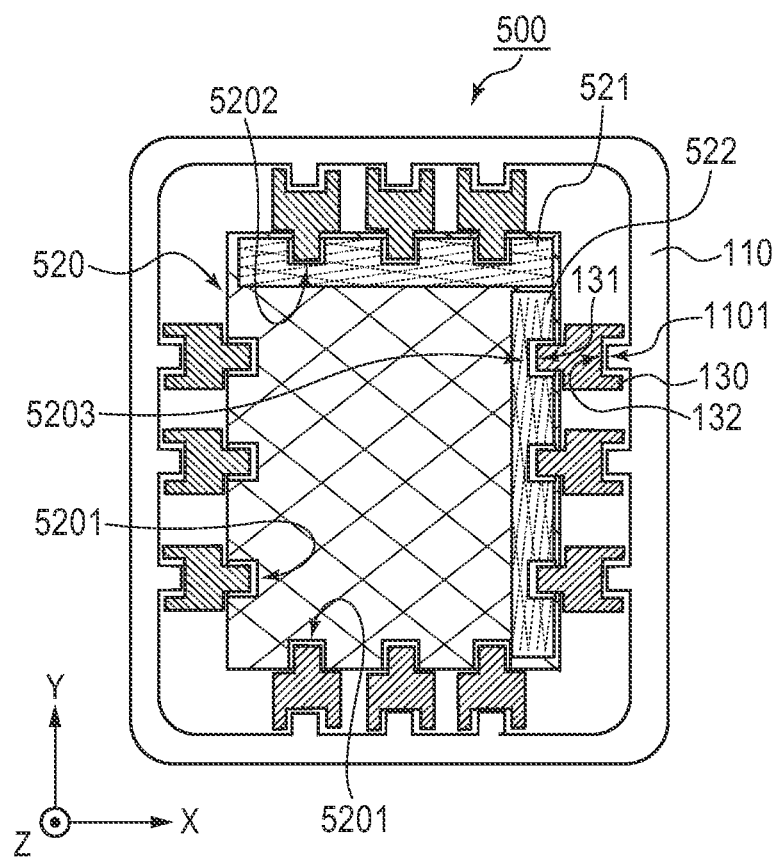
FIG. 11A is a view for illustrating an example of an internal configuration of a radiation imaging apparatus according to a fifth example embodiment of the present disclosure as viewed from a back surface side.

FIG. 11A is a view for illustrating an internal configuration of an imaging apparatus 500 as seen from a back surface side.

The imaging apparatus 500 includes the exterior case 110, an internal unit 520, and the fitting members 130. The buffer material 141, the support member 142, the buffer material 150, the flexible boards 160, the IC boards 170, the electric board 180, and the signal processing board 190 are provided inside the exterior case 110.

The internal unit 520 includes the detector 121, the base plate 124, the flexible boards 160, and the electric board 180. The internal unit 520 further includes, on a side closer to the back-surface-side case portion 112 than the electric board 180 (see FIG. 2B), protection members 521 and 522. The protection members 521 and 522 are cover components arranged to protect boards (for example, the electric board 180) and, for example, are fixed to the base plate 124 by screws. In the fifth embodiment, the protection members 521 and 522 protect an electric board configured to perform at least one of driving of the detector 121 or processing on electric signals from the detector 121.

The internal unit 520 has recesses (first recess) at end portions thereof, specifically, recesses 5201 formed in end portions of the base plate 124, recesses 5202 formed in an end portion of the protection member 521, and recesses 5203 formed in an end portion of the protection member 522. In this case, the recesses 5201 are not formed in the end portions of the base plate 124, specifically, at the upper side of the internal unit 520 with the protection member 521 and at the right side of the internal unit 520 with the protection member 522. At each of the left side and the lower side of the internal unit 520 without the protection members 521 and 522, a mode in which the protrusions 131 of the fitting members 130 are fitted to the recesses 5201 formed in the end portions of the base plate 124 is adopted. Moreover, at the upper side of the internal unit 520 with the protection member 521, the protrusions 131 of the fitting members 130 are fitted to the recesses 5202 formed in the end portion of the protection member 521. Further, at the right side of the internal unit 520 with the protection member 522, the protrusions 131 of the fitting members 130 are fitted to the recesses 5203 formed in the end portion of the protection member 522.

Here, the mode in which the protrusions 131 of the fitting members 130 are fitted to the recesses 5201 formed in the end portions of the base plate 124 in addition to the recesses 5202 and 5203 formed in the end portions of the protection members 521 and 522 is illustrated. Meanwhile, protection members each having recesses in an end portion may be provided at all of the four sides, specifically, upper, lower, left, and right sides of the internal unit 520, and the recesses formed in the end portions of the protection members and the protrusions 131 of the fitting members 130 may be fitted at each of the four sides of the internal unit 520.

Moreover, the fitting members 130 (including the fitting members 230 to 430 in the second to fourth embodiments described above) may be made of a material such as a resin, rubber, or elastomer having elasticity (that is, elastic body) and being non-conductive (that is, non-conductive body). Moreover, the fitting members 130 may each be made of a material such as metal having no elasticity when a material having elasticity is used as a material of a mating member. When a conductive material such as metal is used as a material of the fitting members 130, it is required that an insulating member be provided at least between the incident-side case portion 111 and the back-surface-side case portion 112 or between the fitting members 130 and the internal unit 520. Moreover, the fitting members 130 arranged at a plurality of locations are all made of the same material, but the material may be changed depending on locations at which the fitting members 130 are arranged. For example, at the corner portions of the exterior case 110, the fitting members 130 having a hardness higher than those of the fitting members 130 provided at other locations may be arranged. With such arrangement, not only the movement of the internal unit 120 due to the inertial force generated at the time of falling but also deformation of the radiation incident-side case portion 111 and the back-surface-side case portion 112 can be prevented.

Figure 11B:
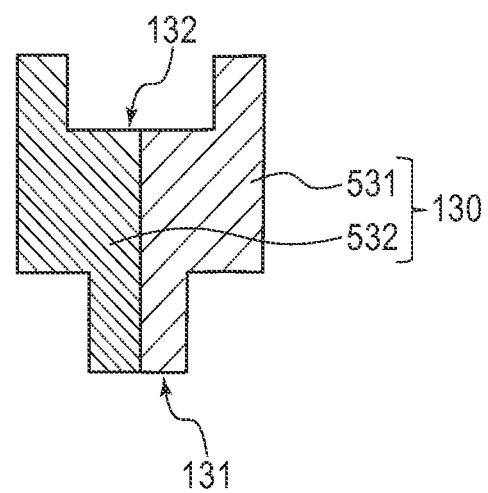
FIG. 11B is a view for illustrating an example of a fitting member made of different materials.

Further, as illustrated in FIG. 11B, one fitting member 130 may have a plurality of regions 531 and 532 made of different materials. Specifically, the fitting member 130 may be made of different materials in the region 531 at the right portion and the region 532 at the left portion. In FIG. 11B, the example in which the fitting member 130 is made of different materials in the right and left regions is illustrated. However, the fitting member 130 may be made of different materials in the up-and-down direction (that is, on the side of the radiation incident-side case portion 111 and on the side of the back-surface-side case portion 112). Moreover, the fitting member 130 may be made of two or more kinds of materials, or may be made of the same material and have different hardness.

Sixth Example Embodiment

Next, a sixth example embodiment of the present disclosure is described. In the following description of the sixth embodiment, a description of matters which are common to the first to fifth embodiments described above is omitted, and matters different from those of the first to fifth embodiments are described.

Figure 12:
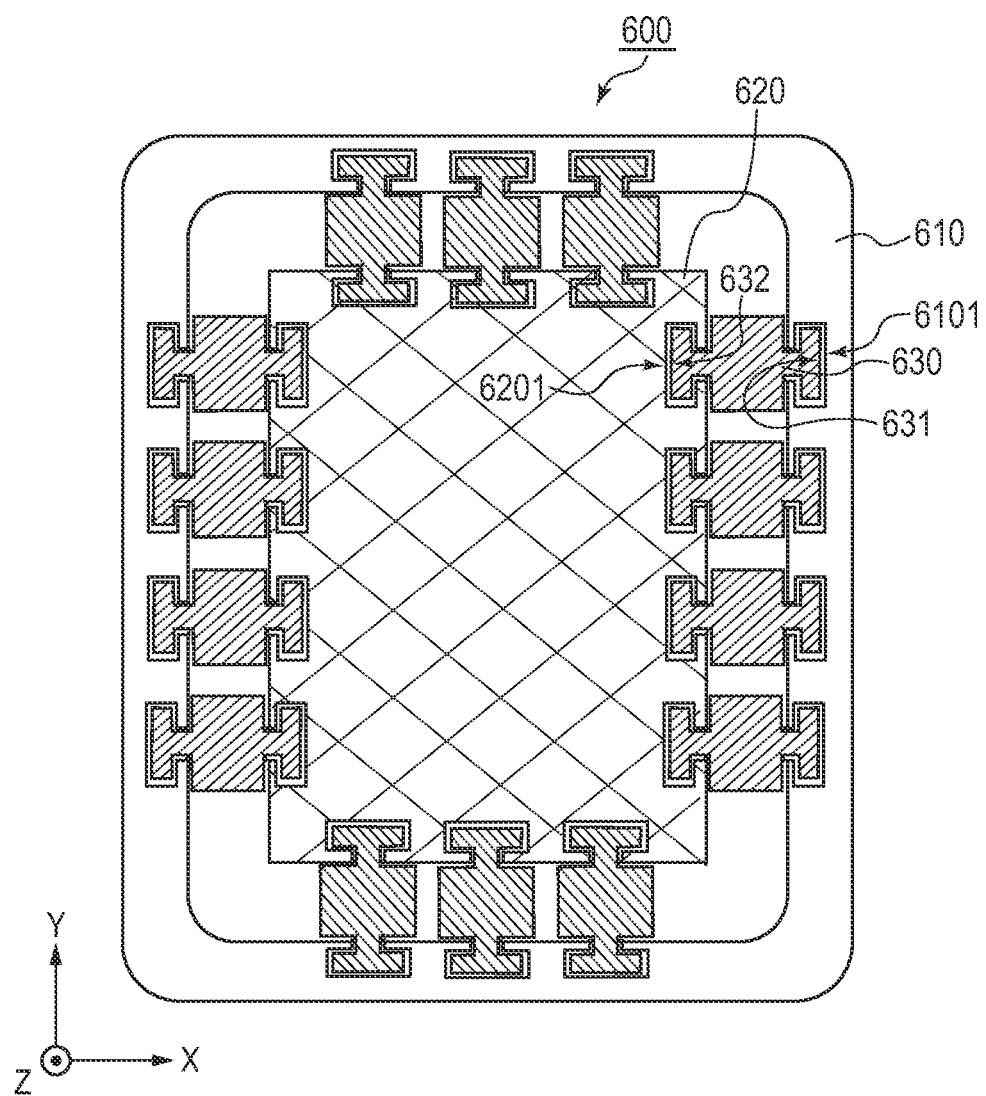
FIG. 12 is a view for illustrating an example of an internal configuration of a radiation imaging apparatus according to a sixth example embodiment of the present disclosure as seen from a back surface side.

FIG. 12 is a view for illustrating an internal configuration of an imaging apparatus 600 as seen from a back surface side.

An exterior case 610 corresponds to the exterior case 110 illustrated in FIG. 1 but is different from the exterior case 110 in that the exterior case 610 has a plurality of modified recesses (first recess) 6101 formed in inner walls thereof.

An internal unit 620 corresponds to the internal unit 120 illustrated in FIG. 1 but is different from the internal unit 120 in that the internal unit 620 has a plurality of modified recesses (second recess) 6201 formed in end portions thereof. The internal unit 620 includes the detector 121 and the base plate 124. However, in the sixth embodiment, recesses corresponding to the modified recesses 6201 formed in the end portions of the internal unit 620 are formed in the end portions of the base plate 124.

The fitting members 630 correspond to the fitting members 130 illustrated in FIG. 1 but are different from the fitting members 130 in that the fitting members 630 each have a modified protrusion (first protrusion) 631 and a modified protrusion (second protrusion) 632. Specifically, the modified protrusions 631 of the fitting members 630 are fitted to the modified recesses (first recess) 6101 formed in the inner walls of the exterior case 610, and the modified protrusions 632 are fitted to the modified recesses (second recess) 6201 formed in the end portions of the internal unit 620.

The imaging apparatus 600 may include the buffer material 141, the support member 142, the buffer material 150, the flexible boards 160, the IC boards 170, the electric board 180, and the signal processing board 190 inside the exterior case 610.

Figure 13:
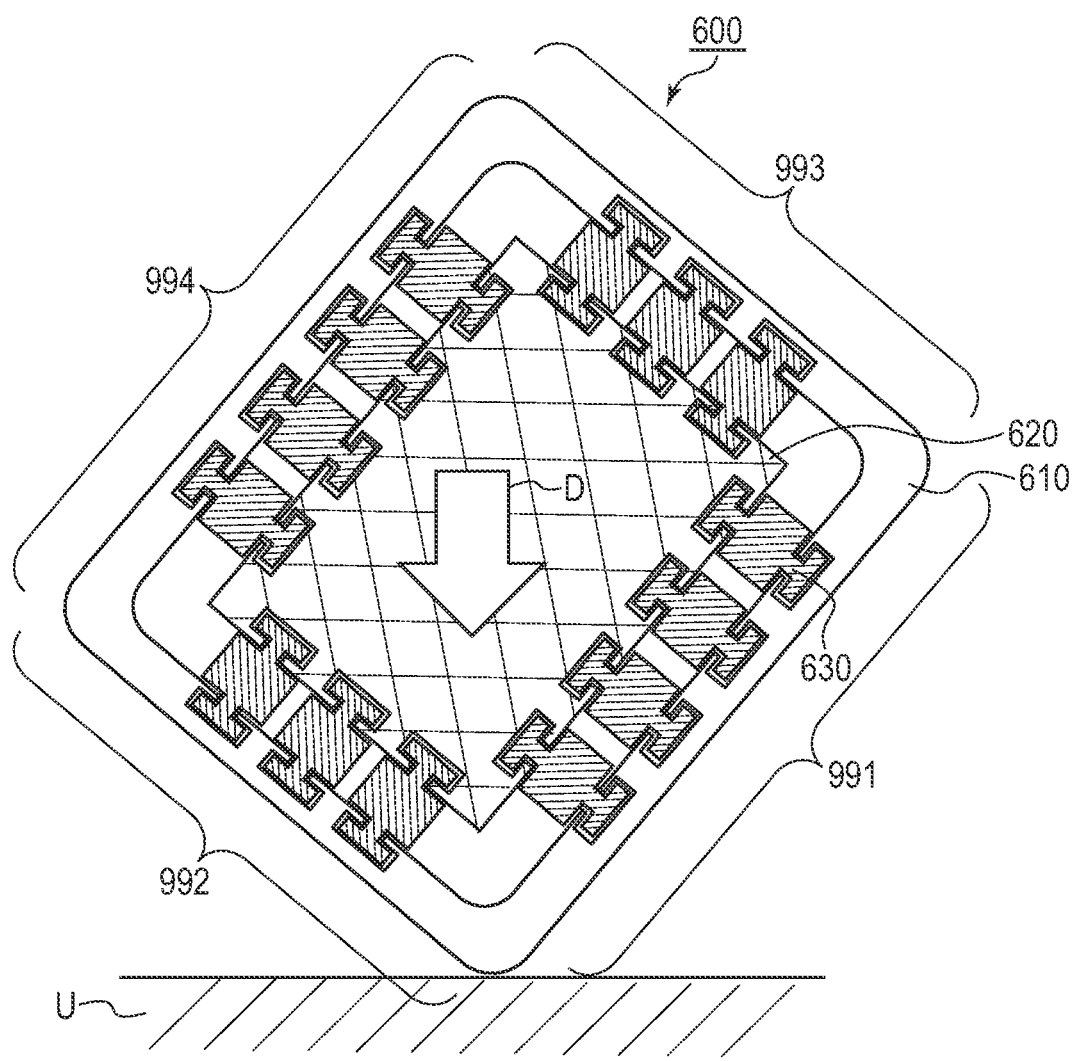
FIG. 13 is a view for illustrating an example of a state in which a corner portion of the radiation imaging apparatus illustrated in FIG. 12 falls in a vertical direction toward the floor.

Similarly to FIG. 4B, FIG. 13 is an illustration of a state in which a corner portion of the imaging apparatus 600 is in contact with the floor surface of the floor U.

In the imaging apparatus 100 according to the first embodiment, the stress generated by the inertial force generated inside at the time of falling is absorbed in the compression direction by the fitting members 130 or the like. Meanwhile, in the imaging apparatus 600 according to the sixth embodiment, the movement of the internal unit 620 can be regulated not only in the compression direction but also in a tensile direction at the time of falling. Moreover, in the imaging apparatus 100 according to the first embodiment, the movement of the internal unit 120 is prevented mainly at a side 991 and a side 992. Meanwhile, in the imaging apparatus 600 according to the sixth embodiment, the internal unit 620 can be regulated also with the fitting members 630 arranged at a side 993 and a side 994. Accordingly, the impact can be received in a distributed manner by all of the fitting members 630.

In the sixth embodiment, the mode in which the modified recesses (first recess) 6101 are formed in the inner walls of the exterior case 610 and the modified recesses (second recess) 6201 are formed in the end portions of the internal unit 620 and in which the modified protrusions (first protrusion) 631 and the modified protrusions (second protrusion) 632 to be fitted to the modified recesses are formed on the fitting members 630 is illustrated. However, a mode in which the relationship between the modified protrusions and the modified recesses in relation to the fitting is reversed may be adopted. In the case of this mode, the modified protrusions (first protrusion) are formed on the inner walls of the exterior case 610 and the modified protrusions (second protrusion) are formed on the end portions of the internal unit 620, and the modified recesses (first recess and second recess) to be fitted to those modified protrusions are formed in the fitting members 630.

Seventh Example Embodiment

Next, a seventh embodiment of the present disclosure is described. In the following description of the seventh embodiment, a description of matters which are common to the first to sixth embodiments described above is omitted, and matters different from those of the first to sixth embodiments are described.

Figure 14:
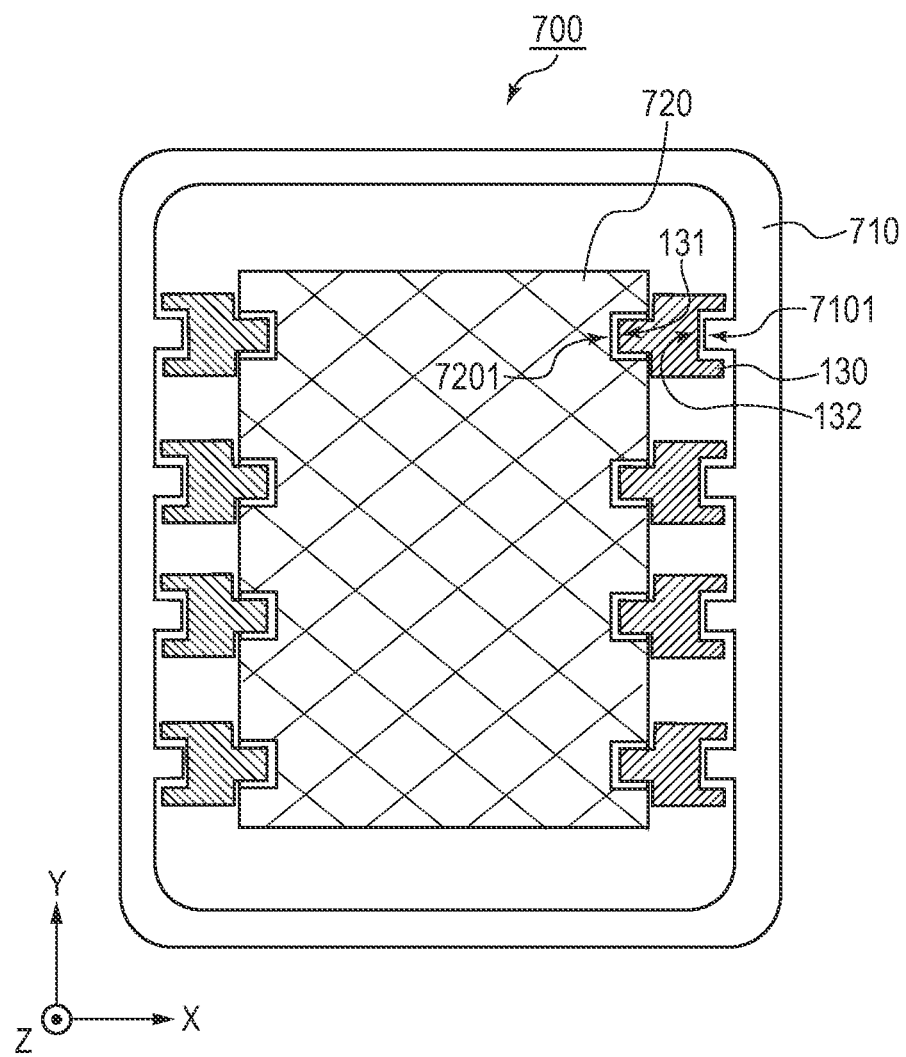
FIG. 14 is a view for illustrating an example of an internal configuration of a radiation imaging apparatus according to a seventh example embodiment of the present disclosure as seen from a back surface side.

FIG. 14 is a view for illustrating an internal configuration of an imaging apparatus 700 as seen from a back surface side.

An exterior case 710 corresponds to the exterior case 110 illustrated in FIG. 1 but is different from the exterior case 110 in that the exterior case 710 has a plurality of protrusions (first protrusion) 7101 formed only on the inner walls at the right and left sides of the exterior case 710. In other words, the exterior case 710 is different from the exterior case 110 in that the protrusions (first protrusion) 7101 are not formed on the inner walls at the upper and lower sides of the exterior case 710.

An internal unit 720 corresponds to the internal unit 120 illustrated in FIG. 1 but is different from the internal unit 120 in that the internal unit 720 has a plurality of recesses (first recess) 7201 formed only in the end portions at the right and left sides of the internal unit 720. In other words, the internal unit 720 is different from the internal unit 120 illustrated in FIG. 1 in that the recesses (first recess) 7201 are not formed in the end portions at the upper and lower sides of the internal unit 720.

The seventh embodiment is different from the first embodiment in that the fitting members 130 are provided only at the right and left sides of the internal unit 720. That is, the fitting members 130 are not provided at the upper and lower sides of the internal unit 720. Moreover, in the seventh embodiment, for example, under a condition in which the falling direction is uniquely determined, the fitting members 130 may be arranged at only three sides among the four sides of the internal unit 720.

As described above, according to the present disclosure, at least one or more fitting members may be arranged at each of at least two sides among the four sides of the substantially quadrilateral shape of the internal unit.

According to the present disclosure, when an impact due to falling is received, the movement of the internal unit can be appropriately regulated, thereby being capable of improving impact resistance. Accordingly, protection of the detector provided inside the imaging apparatus can be enhanced.

While the present disclosure has been described with reference to example embodiments, it is to be understood that the disclosure is not limited to the disclosed example embodiments. The scope of the following claims is to be accorded the broadest interpretation so as to encompass all such modifications and equivalent structures and functions.

This application claims the benefit of Japanese Patent Application No. 2019-080006, filed Apr. 19, 2019 which is hereby incorporated by reference herein in its entirety.

What is claimed is:

1. A radiation imaging apparatus comprising:
    an internal unit which has a substantially quadrilateral shape as seen from an incident direction of a radiation including:
        a radiation detector arranged to convert the radiation that is passed through a subject into electric signals; and
        a base plate arranged to support the radiation detector;
    a case having a rectangular parallelepiped shape and arranged to accommodate the internal unit;
    a fitting member interposed between an inner wall of the case and an end portion of the internal unit, and fitted to the inner wall of the case and the end portion of the internal unit in a planar view as seen from an incident direction of the radiation; and
    a plurality of flexible boards arranged at one side of the internal unit,
    wherein at least a part of the fitting member is arranged between the plurality of flexible boards at the one side of the internal unit.

2. The radiation imaging apparatus according to claim 1, the fitting member comprises a plurality of fitting members arranged at each of at least two sides among four sides of the substantially quadrilateral shape of the internal unit.

3. The radiation imaging apparatus according to claim 2, wherein the plurality of fitting members are arranged at all of the four sides.

4. The radiation imaging apparatus according to claim 1, wherein the fitting member is arranged to regulate movement of the internal unit.

5. The radiation imaging apparatus according to claim 4, wherein the fitting member is arranged to regulate movement of the internal unit in an in-plane direction within a plane in a planar view when the internal unit is seen from the incident direction of the radiation.

6. The radiation imaging apparatus according to claim 1, wherein the fitting member is fitted to the inner wall of the case and an end portion of the base plate included in the internal unit.

7. The radiation imaging apparatus according to claim 1, wherein the internal unit further includes an electric board configured to perform at least one of driving of the radiation detector or processing on the electric signals.

8. The radiation imaging apparatus according to claim 7, further comprising a protection member arranged to protect the electric board,
    wherein the fitting member is fitted to the inner wall of the case and an end portion of the protection member included in the internal unit.

9. The radiation imaging apparatus according to claim 1, wherein the inner wall of the case has a first protrusion,
    wherein the end portion of the internal unit has a first recess,
    wherein the fitting member has a second protrusion and a second recess, and
    wherein the second protrusion is fitted to the first recess, and the second recess is fitted to the first protrusion.

10. The radiation imaging apparatus according to claim 9, wherein a part of a side wall of the first recess is inclined, and
    wherein a portion of the second protrusion which is fitted to the part of the side wall of the first recess is inclined.

11. The radiation imaging apparatus according to claim 9, wherein the fitting member has a plurality of second protrusions and a plurality of second recesses.

12. The radiation imaging apparatus according to claim 9, wherein the second protrusion of the fitting member is arranged between the plurality of flexible boards at the one side of the internal unit.

13. The radiation imaging apparatus according to claim 1,
wherein the inner wall of the case has a first recess,
wherein the end portion of the internal unit has a first protrusion,
wherein the fitting member has a second protrusion and a second recess, and
wherein the second protrusion is fitted to the first recess, and the second recess is fitted to the first protrusion.

14. The radiation imaging apparatus according to claim 1,
wherein the inner wall of the case has a first recess,
wherein the end portion of the internal unit has a second recess,
wherein the fitting member has a first protrusion and a second protrusion, and
wherein the first protrusion is fitted to the first recess, and the second protrusion is fitted to the second recess.

15. The radiation imaging apparatus according to claim 1, wherein the fitting member is a non-conductive body.

16. The radiation imaging apparatus according to claim 15, wherein the fitting member is made of a resin or elastomer.

17. The radiation imaging apparatus according to claim 1, wherein the fitting member is an elastic body.

18. The radiation imaging apparatus according to claim 1, wherein the fitting member is formed so as to have a plurality of regions made of different materials.

19. The radiation imaging apparatus according to claim 1,
wherein the fitting members are each provided between a plurality of flexible boards so as to prevent interference with the flexible boards.

20. The radiation imaging apparatus according to claim 1, wherein the fitting member comprises a plurality of fitting members, and the plurality of fitting members are arranged at a side portion except a corner portion of the substantially quadrilateral shape of the internal unit.

* * * * *